(12) United States Patent
Zwart

(10) Patent No.: US 10,448,934 B2
(45) Date of Patent: Oct. 22, 2019

(54) SAMPLING DEVICE AND METHOD FOR PREPARING THE SAME

(75) Inventor: Meindert Durk Zwart, Rosmalen (NL)

(73) Assignee: ROVERS HOLDING B.V., Oss (NL)

( * ) Notice: Subject to any disclaimer, the term of this patent is extended or adjusted under 35 U.S.C. 154(b) by 0 days.

(21) Appl. No.: 13/817,426

(22) PCT Filed: Aug. 17, 2010

(86) PCT No.: PCT/NL2010/050515
§ 371 (c)(1),
(2), (4) Date: May 3, 2013

(87) PCT Pub. No.: WO2011/021931
PCT Pub. Date: Feb. 24, 2011

(65) Prior Publication Data
US 2013/0211288 A1    Aug. 15, 2013
US 2014/0180165 A9    Jun. 26, 2014

(51) Int. Cl.
*A61B 10/04* (2006.01)
*A61B 10/02* (2006.01)
(Continued)

(52) U.S. Cl.
CPC .............. *A61B 10/04* (2013.01); *A61B 10/02* (2013.01); *A61B 10/0291* (2013.01);
(Continued)

(58) Field of Classification Search
CPC ................ A61B 10/04; A61B 10/0291; A61B 2017/00115; A61B 10/02;
(Continued)

(56) References Cited

U.S. PATENT DOCUMENTS 4,498,904 A * 2/1985 Turner .................... A61M 5/24
422/928
4,877,037 A * 10/1989 Ko ..................... A61B 10/0291
600/569

(Continued)

FOREIGN PATENT DOCUMENTS

CN    1177917 A    4/1998
CN    1440255 A    9/2003
(Continued)

OTHER PUBLICATIONS

Espacenet; English Abstract of RU 2307610; worldwide.espacenet.com.

(Continued)

*Primary Examiner* — Patrick Fernandes
(74) *Attorney, Agent, or Firm* — Davis Wright Tremaine LLP; Heather M. Colburn

(57) ABSTRACT

The present invention relates to a sampling device for sampling a body cavity, in particular for sampling the vagina and/or cervix. The sampling device comprises a tube having two open ends, a sample-collecting member and a plunger. The plunger is inserted in the tube, with the distal plunger end protruding from the distal tube end, and carries the sample-collecting member at the proximal tube end. The plunger is displaceable in the proximal direction in the tube from a retracted introduction position into an extended sampling position. In the introduction position, the sampling member is situated inside the tube and protrudes from the tube in the sampling position.

24 Claims, 11 Drawing Sheets

(51) Int. Cl.
*A61B 17/00* (2006.01)
*A61B 17/42* (2006.01)
*A61B 90/00* (2016.01)

(52) U.S. Cl.
CPC ............ *A61B 2010/0216* (2013.01); *A61B 2017/00115* (2013.01); *A61B 2017/4216* (2013.01); *A61B 2090/034* (2016.02); *A61B 2090/036* (2016.02)

(58) Field of Classification Search
CPC ...... A61B 2019/304; A61B 2010/0216; A61B 2019/306; A61B 2017/4216
USPC ........................................................ 600/569
See application file for complete search history.

(56) References Cited

U.S. PATENT DOCUMENTS

| | | | | |
|---|---|---|---|---|
| 5,339,828 | A * | 8/1994 | Keating | A61B 10/04 600/572 |
| 5,445,164 | A * | 8/1995 | Worthen | A61B 10/0291 600/572 |
| 5,795,309 | A * | 8/1998 | Leet | A61B 10/0291 600/569 |
| 6,099,547 | A | 8/2000 | Gellman et al. | |
| 6,302,853 | B1 * | 10/2001 | Sak | A61B 10/0291 600/569 |
| 6,860,162 | B1 * | 3/2005 | Jaeger | G01N 1/12 73/863.85 |
| 2002/0016556 | A1 | 2/2002 | Williams | |
| 2006/0235444 | A1 | 10/2006 | Huitema et al. | |
| 2008/0188769 | A1 | 8/2008 | Lu | |
| 2009/0177114 | A1 * | 7/2009 | Chin | A61B 10/04 600/565 |
| 2011/0144534 | A1 * | 6/2011 | Gombrich | A61B 10/0291 600/572 |

FOREIGN PATENT DOCUMENTS

| | | |
|---|---|---|
| EP | 0031228 A1 | 7/1981 |
| EP | 0612503 A1 | 8/1994 |
| EP | 0763345 A1 | 3/1997 |
| RU | 2307610 | 10/2007 |
| WO | 98/22030 | 5/1998 |
| WO | 2003/026502 A1 | 4/2003 |

OTHER PUBLICATIONS

Espacenet; English Abstract of CN1177917(A); worldwide.espacenet.com.

Espacenet; English Abstract of CN1440255(A); worldwide.espacenet.com.

Office Action, dated Jul. 25, 2017, received in European Application No. 10 747 325.

International Search Report and Written Opinion received in International Application No. PCT/NL2010/050515, dated Nov. 11, 2010, 8 pages.

* cited by examiner

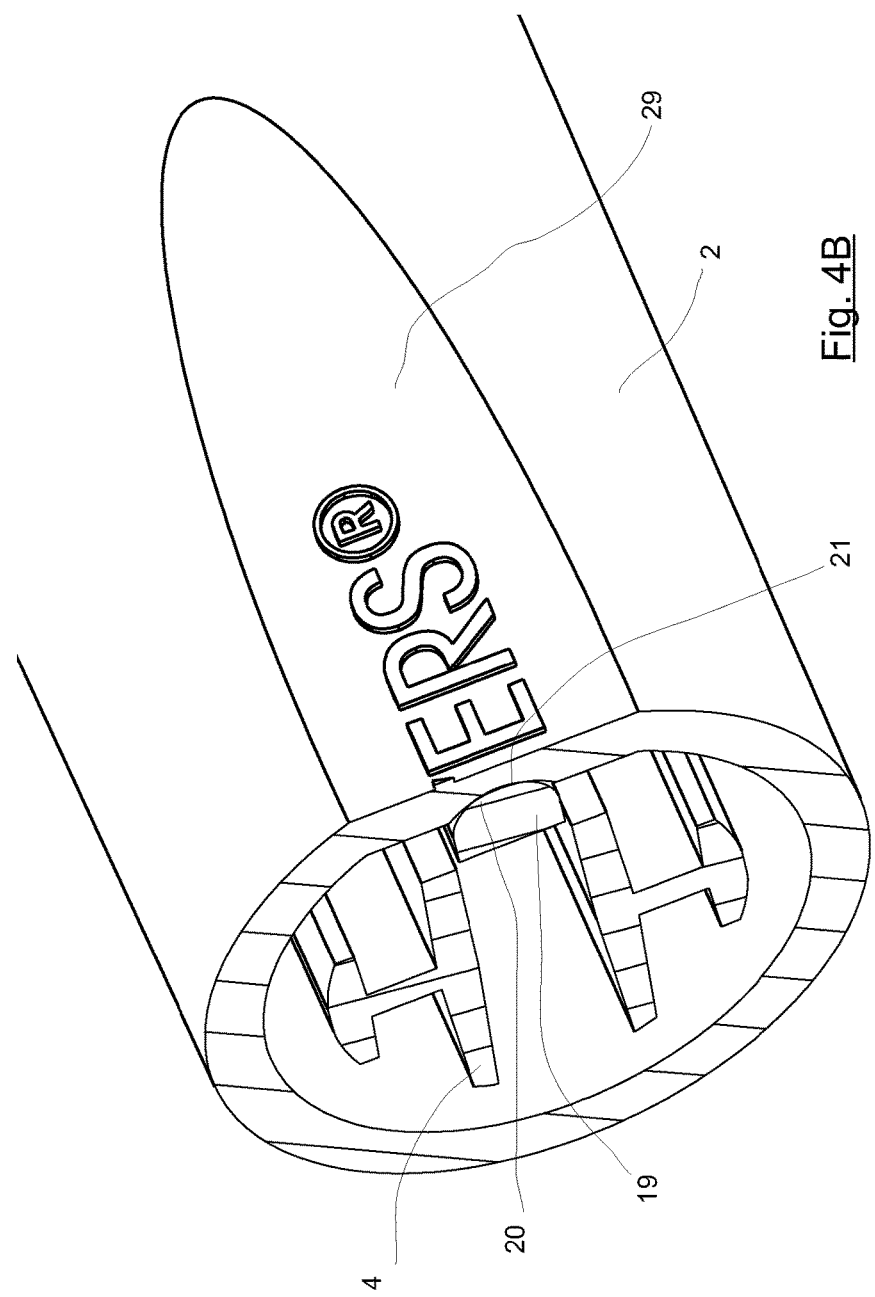

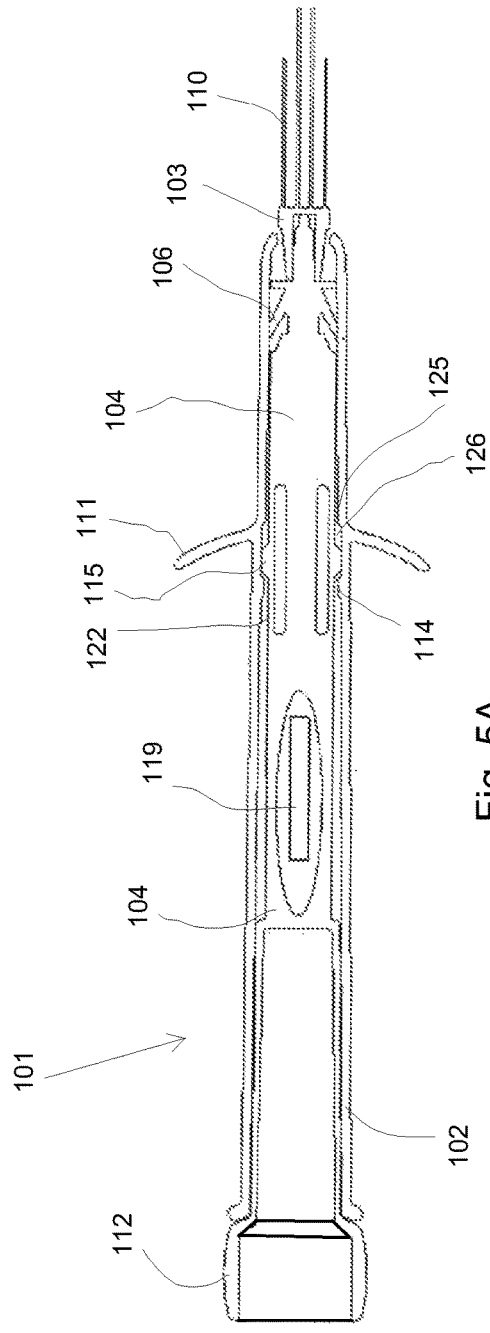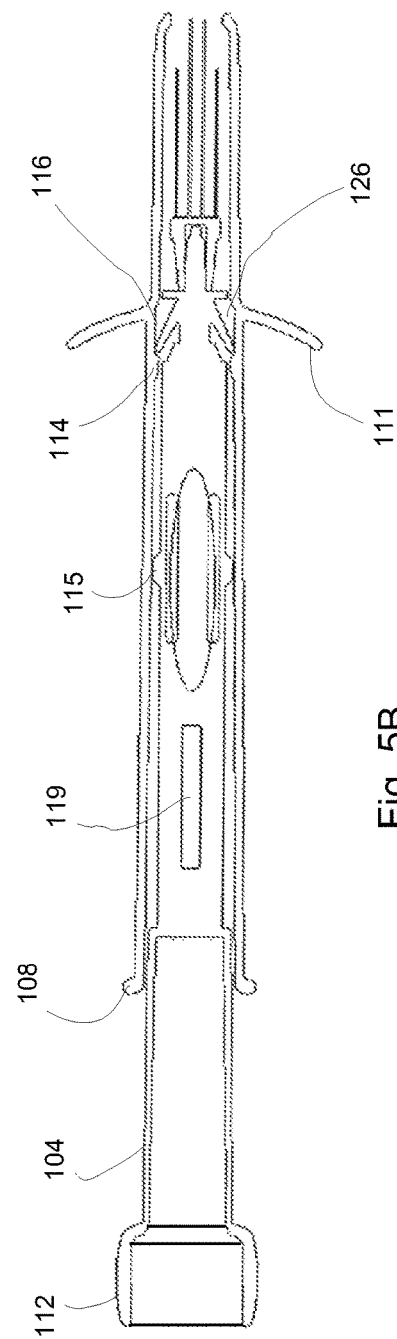
Fig. 5A
Fig. 5B

SAMPLING DEVICE AND METHOD FOR PREPARING THE SAME

BACKGROUND OF THE INVENTION

Field of the Invention

The present invention relates to a sampling device for sampling a body cavity, in particular for sampling the vagina and/or cervix.

Description of the Related Art

Such sampling devices are known. Examples which may be mentioned include, inter alia, the Cervex-Brush®, the EndoCervex-Brush® and the Viba-Brush®, which are all marketed by Rovers Medical Devices B.V. (NL).

The Viba-Brush® is a brush having a plurality of relatively long brush hairs which extend in the axial direction. One end of each of these brush hairs is fixed on the hair carrier, while the other end protrudes forward freely in the proximal direction. Together, the hairs form a bundle of hairs which extend mutually parallel. In the horizontal position—when the brush hairs extend horizontally—these hairs continue to extend substantially horizontally; each of them forms a so-called 'cantilever beam'. These brush hairs do not have to be supported, as, due to the fact that the brush hairs in this case form cantilever beams, they automatically continue to extend mutually parallel and in the axial direction.

The EndoCervex-Brush® is a spike extending in the axial direction and comprising a plurality of relatively short brush hairs running in the transverse direction. One end of these brush hairs is also fixed to the spike which serves as a carrier and the other end is a free end. Also, in this case as well, the brush hairs form cantilever beams so that when the brush hairs are oriented horizontally, the brush hairs will also continue to extend substantially horizontally.

When collecting a sample from the vagina and/or cervix, the sampling device, that is to say the sampling member arranged on a stick thereof, such as the abovementioned Viba-brush® or EndoCervex-brush®, is inserted into the vagina in order to then collect a sample. Such sampling is usually carried out by a third party, such as a physician or an assistant physician. Many women do not like the idea of such a sampling, because they do not feel comfortable with such a procedure. A solution to this problem could be self-sampling, where the woman carries out sampling herself.

WO 03/026502 discloses a device for sampling cervical tissue. According to the publication, this device is intended for self-sampling. The sampling procedure is very complicated, however. Between page 9, line 24-page 10, line 11 and page 18, line 7-page 19, line 7, WO 03/026502 twice describes how a pre-insertion assembly is formed by placing an introduction guide member 20 into the insertion tube 2, this combination is then introduced into the vagina, and the introduction guide member 20 is subsequently removed from the insertion tube, the insertion tube 2 is then introduced further into the vagina, and when the insertion tube 20 has been positioned correctly, the cervical sampler 50—a stick with a sample-collecting member 42 at the proximal end—is pushed through the insertion tube and sampling is carried out. Referring to page 11, line 2 and FIGS. 2 and 5, the insertion tube is provided at the distal end—that is to say at the end facing away from the body of the woman—with a sealing flange with a centrally arranged bore which is narrow compared to the diameter of the insertion tube and through which the stick of the introduction guide member extends in the position in FIG. 2 and through which the stick of the cervical sampler 50 extends in the position from FIG. 5. However, due to the wide head 32 and the wide support member 23, both of which form an integral part of the stick, it is not possible to remove the introduction guide member 20 from the insertion tube 2. Also, due to the wide aligning members, both of which form an integral part of the stick 55, it is not possible to insert the cervical sampler into the insertion tube 2. The device described in WO 03/026502 is thus ineffective and can therefore not function as described in WO 03/026502. In so far as the device according to WO 03/026502 can be used for sampling, the degree to which the sample-collecting member 42 can be extended outwards from the insertion tube—see FIG. 5—is limited by the fact that the wide handle 56 of the sampler 50 comes to lie against the sealing flange 16 of the insertion tube. However, if the sampler 50 is rotated during taking of the sample—as instructed—then the sample-collecting member can be retracted into the insertion tube and thus lose contact with the tissue to be sampled. Reliable sampling can therefore not be guaranteed. The same applies to the audible and tangible clicking system which is made from a protuberance portion 60 on the handle 56 and the recess 12 in the sealing flange of the insertion tube 2. This should produce a click upon each rotation so that the user can count the number of rotations and know when the sampling has been completed. If the sample-collecting member is retracted during rotation of the sampler 50, the user will not notice any clicking. This also makes sampling reliable. In addition, the design of the clicking system is such that pubic hair can easily become trapped in it, which may lead to painful results during rotation, which may in turn adversely affect the reliability of the sampling. For a good operation of the clicking system and in order to ensure that the sample-collecting member 42 sticks out of the insertion tube 2 during sampling, the handle 56 will have to be pushed continuously during sampling. This is not only impractical and unpleasant, but also means that the tissue to be sampled will be pushed forcefully. This is unpleasant and can lead to unreliable sampling.

SUMMARY OF THE INVENTION

It is an object of the present invention to provide a sampling device for sampling a body cavity, in particular for sampling the vagina and/or cervix, by means of which self-sampling with reliable collection of samples is possible. It should be noted that although the sampling device according to the invention is intended in particular for self-sampling, it is advantageously also highly suitable for sampling by a physician or assistant physician. As is described below, this object can be achieved by various means (aspects), each of which is individually patentable. According to the present application, this object is achieved in particular in accordance with claim 1, which is based on the third aspect (page 5, line 20 ff. of this application).

According to a first aspect of the invention, the abovementioned object is achieved by providing a sampling device for sampling a body cavity, in particular for sampling the vagina and/or cervix, in which the sampling device comprises:
 a tube having an open proximal tube end and an open distal tube end;
 a sample-collecting member;
 a plunger having a proximal plunger end and a distal plunger end;

in which the plunger is inserted in the tube, with the distal plunger end protruding from the distal tube end, and carries the sample-collecting member at the proximal tube end;

in which the plunger is displaceable in the proximal direction in the tube from a retracted introduction position to an extended sampling position;

in which, in the introduction position, the sample-collecting member is situated inside the tube and protrudes from the tube in the sampling position;

in which the sample-collecting member comprises a carrier part and a plurality of brush hairs which protrude from the carrier part in the manner of a cantilever.

Upon insertion into the vagina, also referred to as introduction, the sample-collecting member with cantilever-like brush hairs is retracted in the tube. This prevents these cantilever-like and therefore relatively stiff brush hairs from penetrating into the wall of the vagina or otherwise becoming caught during introduction, which is perceived by the user as unpleasant. The tube protects the wall of the vagina during introduction of the brush hairs. In addition, the tube prevents the brush hairs from stinging if the sampling device is pushed next to the opening of the vagina into the tissue surrounding the opening of the vagina. After the sampling device has been introduced, the sample-collecting member is pushed out of the proximal tube end in the proximal direction by means of the plunger, after which sampling can take place, for example by rotating the sample-collecting member one or more times about the axial longitudinal axis.

It should be noted that U.S. Pat. No. 6,740,049 discloses a brush having a surrounding tube and intended for self-sampling. When the brush is held vertically, that is to say with the hairs hanging down, the brush hairs of the brush extend axially and are retracted inside the tube during introduction. In this case, the brush hairs form a mop (U.S. Pat. No. 6,740,049 uses the terms 'mop-like sampling head' and 'mop-like brush'), that is to say the hairs buckle under their own weight, in other words they are limp threads. By means of a Euler formula, U.S. Pat. No. 6,740,049 indicates how the length from where the hairs form a mop-like brush can be calculated for column-shaped hairs. Such a mop-like brush requires a tube as an introduction aid since the mop-like brush hairs will hang down when the stick is in a horizontal position and introduction into the mouth of the vagina and the vagina itself will thus be difficult. In this case, the tube serves to keep the hairs in an axial position during the introduction procedure. If the brush hairs are cantilever-like, as is the case with the first aspect of the invention, such a tube is not required, as is also evident from the fact that the above-described Viba-Brush® and EndoCervex-brush® are being used by physicians/assistant physicians without such a tube.

According to a further embodiment of the first aspect of the invention, the plurality of brush hairs comprises elongate brush hairs extending in the proximal direction. In the case of self-sampling, elongate cantilever-like brush hairs extending in the proximal direction are particularly suitable for reaching the area around the cervix or the cervix itself after introduction into the vagina. In this case, the elongate brush hairs have a length of in particular at least 15 mm, such as 17 to 35 mm. Brush hairs of such length make good sampling possible.

According to a second aspect of the invention, the object of the invention—providing a sampling device, in particular for self-sampling—is achieved by providing a sampling device for sampling a body cavity, in particular for sampling the vagina and/or cervix, in which the sampling device comprises:

a tube having an open proximal tube end and an open distal tube end;

a sample-collecting member;

a plunger having a proximal plunger end and a distal plunger end;

in which the plunger is inserted in the tube, with the distal plunger end protruding from the distal tube end, and carries the sample-collecting member at the proximal tube end;

in which the plunger is displaceable in the proximal direction in the tube from a retracted introduction position to an extended sampling position;

in which, in the introduction position, the sample-collecting member is situated inside the tube and protrudes from the tube in the sampling position; and in which the tube is provided on the outside with a radially protruding insertion stop which defines the insertion depth over which the tube can be introduced into the body cavity, in particular the vagina, in the proximal direction.

Such an insertion stop prevents on the one hand that the sampling device is introduced too far and, on the other hand, when the insertion stop has come to rest against the body, it indicates to the self-sampling woman—or possibly the sampling third party—that the sampling device has been inserted sufficiently far. In the case of self-sampling, the insertion stop provides assurance to the, usually inexperienced and insecure, self-sampling woman that she is carrying out the sampling correctly.

According to one embodiment of this second aspect of the invention, the insertion depth, measured as the distance from the insertion stop to the proximal end of the tube, is at least 30 mm, in particular 30 to 70 mm. Such a distance, which may be approximately 50 mm, ensures a sufficient insertion depth so that there is still enough space left to push the sampling member out of the tube in order to sample the vagina and/or the cervix. According to yet a further embodiment of the second aspect of the invention, the distance from the insertion stop to the distal end of the tube is at least 5 cm, in particular at least 7 cm, and this distance is in particular 7 to 15 cm. This distance from the insertion stop to the distal end of the tube will be in particular approximately 8 to 10 cm or slightly more. This ensures that, after sampling, the self-sampling woman can readily handle the sampling device during sampling by means of the freely protruding distal end of the tube.

According to a third aspect of the invention, the object of the invention—providing a sampling device particularly suitable for self-sampling—is achieved by providing a sampling device for sampling a body cavity, in particular sampling the vagina and/or cervix, in which the sampling device comprises:

a tube having an open proximal tube end and an open distal tube end;

a sample-collecting member;

a plunger having a proximal plunger end and a distal plunger end;

in which the plunger is inserted in the tube, with the distal plunger end protruding from the distal tube end, and carries the sample-collecting member at the proximal tube end;

in which the plunger is displaceable in the proximal direction in the tube from a retracted introduction position to an extended sampling position;

in which, in the introduction position, the sample-collecting member is situated inside the tube and protrudes from the tube in the sampling position; and in which the sampling device is provided with an extension limiter which defines a maximum extension length over which the sample-collecting member can be extended from the proximal tube end.

This prevents the sample-collecting member from being extended too far out of the proximal tube end and prevents the distal end of the plunger from completely disappearing into the distal end of the tube which would result in it no longer being readily controllable for sampling, and also prevents the sampling device from not being readily removable from the vagina. In the case of self-sampling, the extension limiter provides assurance to the, usually inexperienced and insecure, self-sampling woman that she is carrying out the sampling correctly. According to an embodiment of the third aspect of the invention, the extension length, measured from the proximal end of the sampling device to the proximal tube end, is at least 10 mm, in particular 10 to 45 mm. With such an extension length, the sampling member comes out of the tube to a sufficient degree to ensure good sampling. According to the invention, the extension length may be 25 to 35 mm.

According to the invention, the extension limiter may be designed in various ways. According to a first embodiment, the extension limiter comprises a widened section at the distal plunger end, which widened section comes to a halt against the distal tube end when the sample-collecting member is extended in the proximal direction. By making the widened section non-round with respect to the axial axis of the plunger—such as elongate, viewed transversely to the axial axis—the self-sampling woman can determine the rotary position of the plunger and thus count the number of turns when turning the plunger. According to a second embodiment, which can also be executed in combination with the first embodiment, the extension limiter comprises an extension lock which, viewed in the axial direction of the plunger, fixes the relative position of the plunger with respect to the tube at the maximum extension length. The extension lock ensures that, during sampling, after the maximum extension length has been reached, the position of the plunger and thus also of the sample-collecting member attached to the plunger remains fixed with respect to the tube. Such an extension lock can be constructed in various ways. According to a first embodiment, the extension lock comprises a rib provided inside the tube and extending in the peripheral direction of the tube; and a locking lug provided on the plunger and protruding in the radial direction; the locking lug being resilient and flexible in the radial direction in order to pass the rib in the axial direction. When extending the sample-collecting member, that is to say sliding the plunger in the proximal direction with respect to the tube, the locking lug provided on the plunger will approach the rib provided inside the tube and subsequently pass it due to the fact that the locking lug is resilient and flexible in the radial direction. When the locking lug passes, it will initially be pushed radially inwards and then rebound radially after the rib has been passed and thus will counteract pushing back of the plunger in the distal direction with respect to the tube. However, it should be noted that pushing back of the plunger in the distal direction may be readily possible if sufficient force is used, but this will, however, not happen inadvertently since the locking lug then has to be passed again first. According to another embodiment, the extension lock comprises a lip which runs at an angle with respect to the axial direction and has a free end and a fixed end which is attached to one of either the tube or the plunger; and a first groove in which the free end of said lip can be accommodated and which is provided in the other of either the plunger or the tube. When the plunger is moved with respect to the tube, the lip will then, when it reaches the first groove, snap into the first groove and thus form a lock. In particular when the lip is placed at an angle, this lock can simply be designed such that further extension in the proximal direction is prevented completely while pushing back in the distal direction is not, or hardly, prevented. This embodiment can also be designed such that both further extending in the proximal direction and pushing back in the distal direction are possible, provided a sufficiently large force is exerted to release the lip from the groove again.

According to a fourth aspect, the object of the invention—providing a sampling device, in particular for self-sampling—is achieved by providing a sampling device for sampling a body cavity, in particular for sampling the vagina and/or cervix, in which the sampling device comprises:

a tube having an open proximal tube end and an open distal tube end;
a sample-collecting member;
a plunger having a proximal plunger end and a distal plunger end;

in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position; in which the sampling device is provided with a disassembly restriction, comprising:

a lip which runs at an angle with respect to the axial direction and has a free end and a fixed end which is attached to one of either the tube or the plunger;
a second groove in which the free end of said lip can be accommodated and which is provided in the other of either the plunger or the tube.

Such a disassembly restriction on the one hand makes simple assembly possible in the sense that the proximal end of the plunger can easily be inserted into the distal tube end. On the other hand, such a disassembly restriction effectively prevents a self-sampling woman from inadvertently pulling the plunger out of the tube by operating the plunger in the wrong direction. One of the two parts of this disassembly restriction (that is to say, the lip or the second groove) can also readily form part of an abovementioned extension lock.

According to a fifth aspect of the invention, the object of the invention—providing a sampling device, in particular for self-sampling—is achieved by providing a sampling device for sampling a body cavity, in particular for sampling the vagina and/or cervix, in which the sampling device comprises:

a tube having an open proximal tube end and an open distal tube end;
a sample-collecting member;
a plunger having a proximal plunger end and a distal plunger end;

in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position;

in which the sampling device is furthermore provided with a clicking mechanism which is designed to generate a click when the plunger is rotated through a predetermined angular distance, such as 180° or 360°, with respect to the tube.

Such a clicking mechanism enables the self-sampling woman to check whether she is rotating the sampling member a sufficient number of times during sampling. Each predetermined angular rotation, such as a half or complete turn, of the plunger about the axial axis thereof generates a click. Such a click may be a tangible and/or an audible click. According to the invention, the clicking mechanism may be designed in various ways. According to one embodiment of the invention, the clicking mechanism comprises a clicking bump, such as a clicking groove or a clicking rib, and a radial clicking lug, with the clicking bump on the one hand being provided on one of either the inside of the tube or the plunger and on the other hand the clicking lug being provided on the other of either the plunger or the inside of the tube, in order to generate said click in the sampling position when, during rotation of the plunger with respect to the tube, the clicking lug passes the clicking bump.

According to a sixth aspect of the invention, the object of the invention—providing a sampling device, in particular for self-sampling—is achieved by providing a sampling device for sampling a body cavity, in particular for sampling the vagina and/or cervix, in which the sampling device comprises:
  a tube having an open proximal tube end and an open distal tube end;
  a sample-collecting member;
  a plunger having a proximal plunger end and a distal plunger end;
  a packaging, in particular a sterile packaging;
in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position. Offering the sampling device according to the invention reassures the self-sampling woman that the sampling device is new. The use of sterile packaging furthermore ensures that the sampling device is free from infectious germs.

According to a further embodiment of the sixth aspect of the invention, the sampling device according to the invention has a supply position, in which the plunger protrudes from the proximal tube end, preferably is substantially outside the tube; the plunger is displaceable in the distal direction with respect to the tube from the supply position to said introduction position; and the sampling device is packaged in the packaging in the supply position, the packaging preferably being carried out in a sterile manner. The self-sampling woman can thus inspect the sampling member herself before using the sampling device. Following inspection, the self-sampling woman—or possibly a third party—will then pull back the plunger in order to pull back the sample-collecting member in the tube in order to then insert the sampling device which is in the introduction position, collect a sample and subsequently remove the sampling device from the vagina again. According to a further embodiment, the packaging is transparent in this case. Thus, the self-sampling woman can see the sampling member and consequently inspect it before opening the packaging.

According to a seventh aspect, the invention relates to a method for preparing the sampling device according to the invention, comprising the following steps:
  an unwrapping step in which the sampling device is removed from the packaging;
  an inspection step in which the sampling member, before or after the unwrapping step, is inspected by the patient to be sampled, with the sampling member protruding from the tube during the inspection step;
  a retraction step in which the sampling member, by displacing the plunger in the distal direction with respect to the tube, is retracted into the tube into said introduction position, with the retraction step taking place after the inspection step.

With this seventh aspect, the sampling can be carried out by either the woman to be sampled herself (self-sampling) or by a third party, such as the physician or assistant physician. In both cases, it is reassuring for the woman to be sampled if she can inspect the sampling member before it is being inserted.

According to an eighth aspect of the invention, the object of the invention is achieved by providing a sampling device for sampling a body cavity, in particular for sampling the vagina and/or cervix, in which the sampling device comprises:
  a tube having an open proximal tube end and an open distal tube end;
  a sample-collecting member;
  a plunger having a proximal plunger end and a distal plunger end;
in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position;
in which the outside of the tube, at least the outside of the tube in the part of the tube which is proximal to the insertion stop, is provided with a slippery layer.

The slippery layer, which when in contact with the inside of the vagina provides sliding action, facilitates insertion. The slippery layer can be produced by applying a lubricant, for example those known for condoms, or by choosing a material for the tube and/or a surface structure thereof such that it acts as a slippery layer (or lubricant). Such materials and surface structures are known to those skilled in the art, inter alia from tampon applicators. This eighth aspect of the invention is particularly advantageous in combination with one or more of the other aspects of the invention.

As will be clear, due to these measures, the sampling device according to the first, second, third, fourth, fifth, sixth and seventh aspects of the invention is not only very suitable for self-sampling, but these measures also offer advantages in the case of sampling by third parties, such as a physician or assistant physician, since the risk of the cantilever-like brush hairs stinging in an irritating manner or getting caught during the insertion procedure is reduced (first aspect), a correct insertion depth is readily ensured without requiring the use of an investigative tool such as a speculum (second aspect), a correct extension length is readily ensured (third aspect), inadvertent disassembly is readily prevented (fourth aspect), a sufficient number of rotations of the sample-collecting member can easily be verified (fifth aspect), and inspection of the sample-collecting member by the woman to be sampled is readily possible prior to sampling (sixth aspect). Furthermore, it will be clear that with the second, third, fourth, fifth, sixth and seventh aspects of the invention, other sample-collecting members than the sample-collecting members having cantilever-like brush hairs can readily be used, and even sample-collecting members without brush hairs are conceivable. Moreover, it will also be clear that the first, second, third, fourth, fifth, sixth and seventh aspect of the invention can be applied completely separately from one another as well as in various combinations with one another.

In particular, the sampling device according to the invention is very suitable for sampling the uterus and/or cervix. This sampling may be carried out for various different tests, such as, usually cytological, tests for cancer of the uterus or cervix, tests for infection with HPV (Human Papilloma Virus), or other tests. For tests for cancer of the uterus, it is usually important to collect cell material from the cervix. In that case, the sampling member has to reach the cervix or possibly enter the latter in order to sample the cervix. For HPV tests, it is not absolutely necessary to sample the cervix, as the inventor has found. It has been found that tests for HPV can also readily be carried out on the basis of samples taken from the vagina and without the need to sample the cervix as well. According to the invention, it is very important with HPV tests that the sample is taken from the deeper regions of the vagina, preferably in the vicinity of the cervix, and not from the region of the vagina which is situated at the front, at the mouth of the vagina.

BRIEF DESCRIPTION OF THE SEVERAL VIEWS OF THE DRAWING(S)

The present invention will be described in more detail below with reference to the drawing in which:

FIG. 5 shows a longitudinal section of a sampling device according to a further embodiment of the invention, with FIG. 5A showing the sampling device in the sampling position and FIG. 5B in the introduction position;

DETAILED DESCRIPTION OF THE INVENTION

Figure 1A:
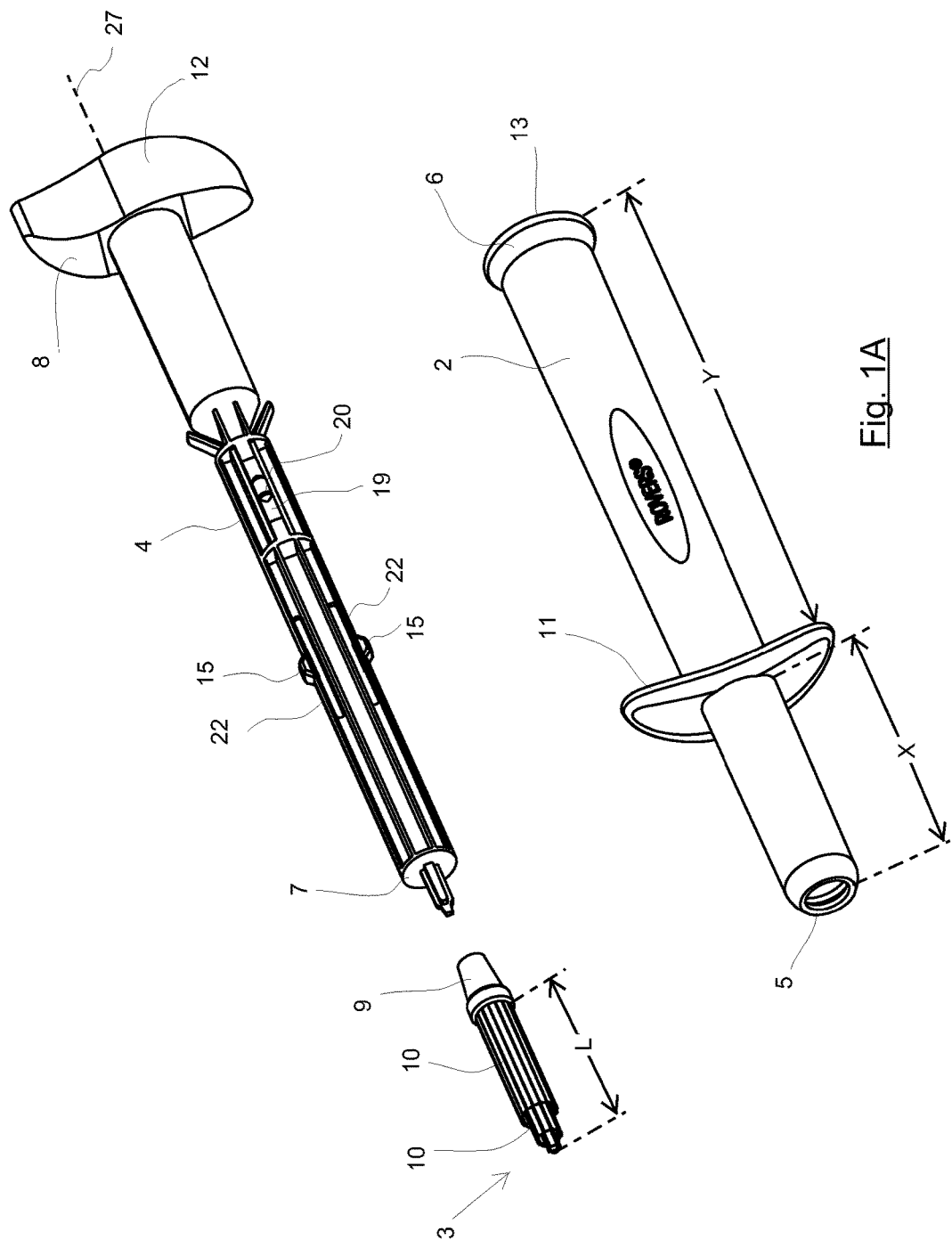
FIG. 1 shows a perspective view of a sampling device according to the invention, with FIG. 1A showing the sampling device with the parts separated and FIG. 1B showing the sampling device in assembled form, in the supply position.

It should be noted that with the sampling device 101 according to the invention illustrated in FIG. 5, the same reference numerals have been used as in the embodiment according to FIGS. 1-4, but increased by 100. So, for example: reference numeral 104 in FIG. 5 corresponds to reference numeral 4 in FIGS. 1-4, with both 104 and 4 denoting the plunger.

Figure 1B:
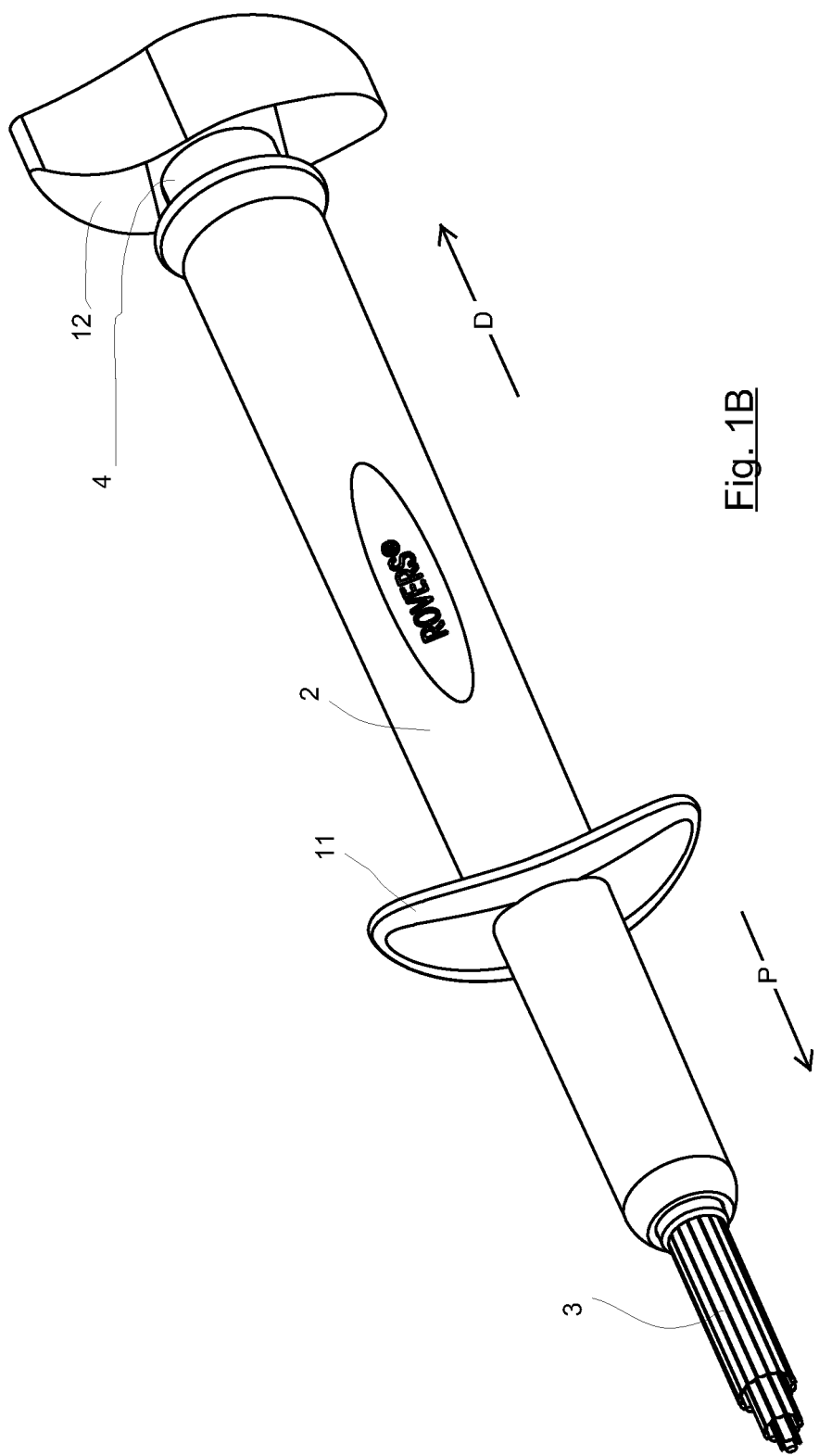

FIG. 1 shows a sampling device 1 according to the invention with the parts separated—FIG. 1A—and in the assembled state—FIG. 1b. According to all aspects of the invention:

the sampling device 1 comprises a tube 2, a sampling member 3 and a plunger 4 having a longitudinal axis 27;

the tube 2 has an open proximal tube end 5 and an open distal tube end 6;

the plunger 4 has a proximal plunger end 7 and distal plunger end 8; and the proximal plunger end 7 carries, optionally in a detachable manner, the sampling member 3.

In the assembled state, the plunger 4 is inserted in the tube 2 and the plunger end 8 protrudes from the distal tube end. The plunger 4 is displaceable in the proximal direction P from a retracted introduction position—see FIG. 2 —, in which the sample-collecting member 3 is inside, preferably completely inside, the tube 2, to an extended sampling position—FIG. 3—in which the sampling member protrudes from the tube 2—in which case the sampling member can, if desired, be completely outside the tube 2.

With respect to all aspects of the invention, except for the first aspect, the sample-collecting member 3 can be of any type with or without brush hairs. The sample-collecting member may, for example, be designed as a foam structure, made of polyurethane foam for example, or as a spatula, made of wood or another material for example. According to the first aspect of the invention, the sample-collecting member 3 comprises cantilever-like brush hairs 10. Corresponding to the other aspects of the invention as well, the sample-collecting member may comprise cantilever-like brush hairs 10.

The cantilever-like brush hairs 10 are attached to a carrier part 9 and in particular elongate and extend in particular in the axial direction. However, it is also conceivable for the cantilever-like brush hairs to extend transversely to the longitudinal direction of the plunger 4 or obliquely with respect to the longitudinal direction of the plunger 4. In the illustrated embodiment with elongate, axial brush hairs 10, the length L thereof is at least 15 mm and in particular 17-25 mm, such as approximately 20 mm. By means of such a sample-collecting member with elongate, axial cantilever-like brush hairs having a length in the range from 25 to 35 mm—(as can be seen in the drawings, the brush hairs do not have to be of equal length)—the vagina and/or cervix can readily be sampled in order to test for HPV (Human Papilloma Virus).

Figure 6:
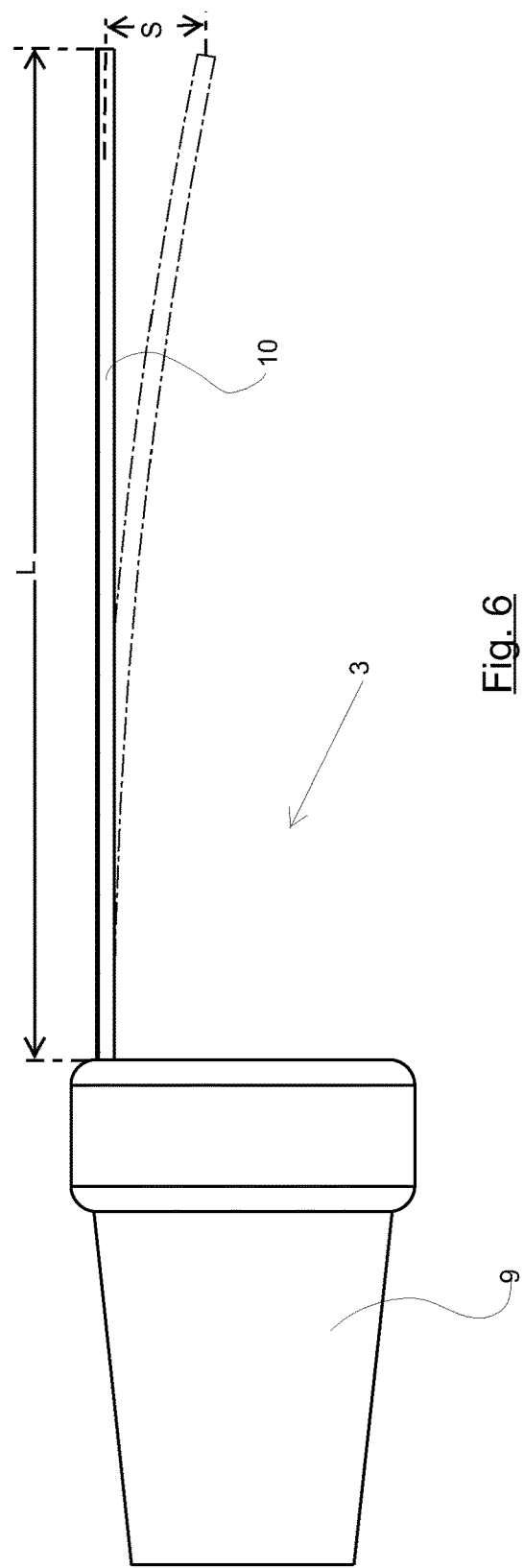
FIG. 6 shows a highly diagrammatical longitudinal side view of the sampling member.

The term cantilever-like brush hairs is understood to mean that the brush hairs form so-called 'cantilever beams' where the longitudinal direction of the brush hairs extends horizontally. Since the brush hairs here form cantilever beams, they will automatically extend horizontally in the horizontal position, without requiring additional support to achieve this. Thus, they do not bend and do not buckle under their own weight This is explained in FIG. 6. FIG. 6 shows a highly diagrammatic representation of the sample-collecting member 3 with only one single brush hair 10 (the other brush hairs have not been illustrated). As shown, the brush hair 10, in the horizontal position, will naturally remain substantially horizontal, although some bending due to its own weight—indicated by the dashed lines—is possible. With cantilever brush hairs according to the invention, the 'bending' under their own weight will be in particular at most 15%, more particularly at most 10%, for example at most 5%. Referring to FIG. 6, the 'bending' is defined here, in the horizontal position of the brush hair, as S/L (in %), with L (in mm) being the length of the brush hair and S (in mm) being 'the vertical deflection of the free end of the brush hair on account of the own weight of the brush hair'.

Figure 2A:
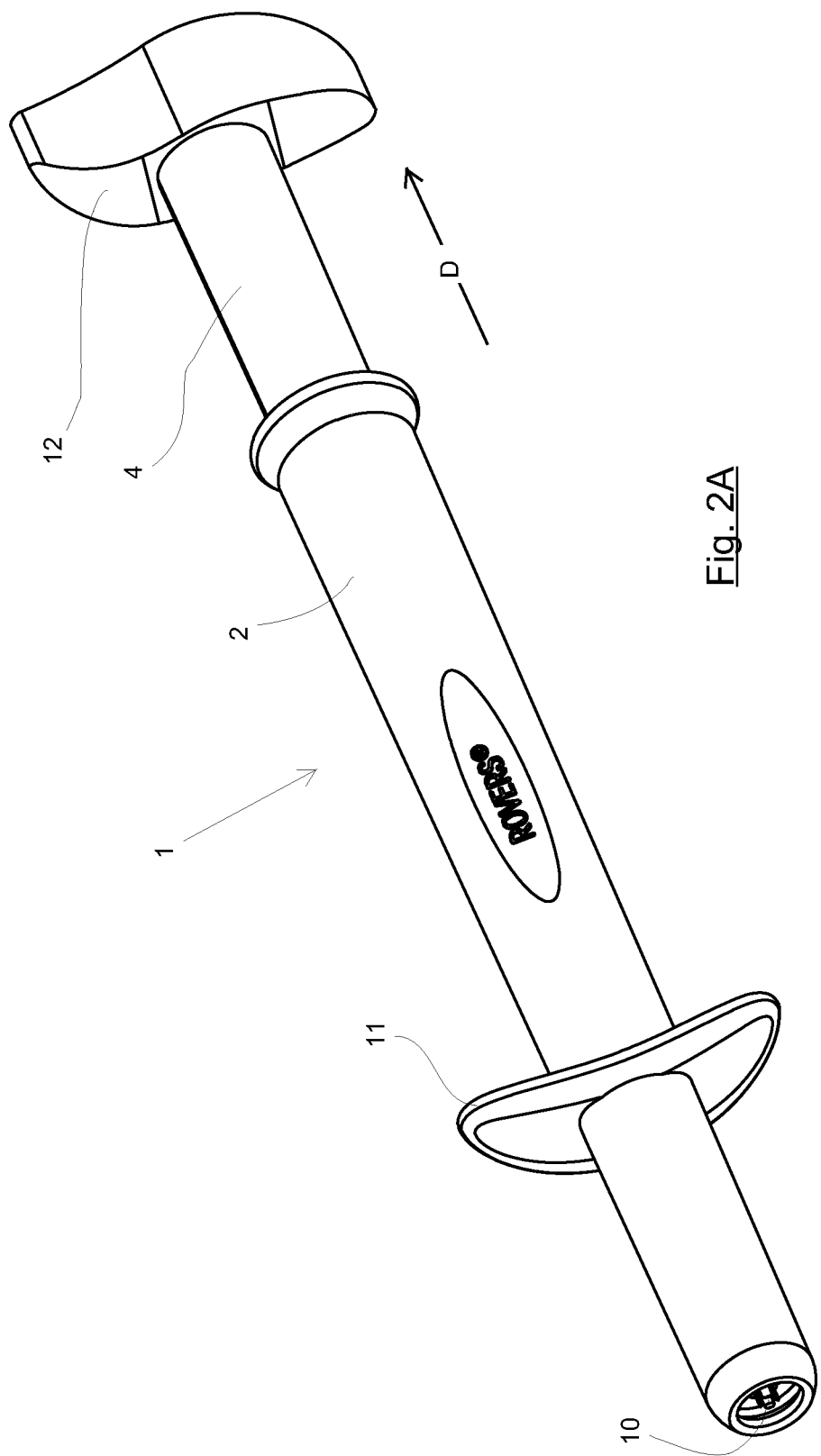
FIG. 2 shows the sampling device from FIG. 1 in the so-called introduction position; with FIG. 2A being a perspective view and FIG. 2B being a perspective longitudinal section.
Figure 2B:
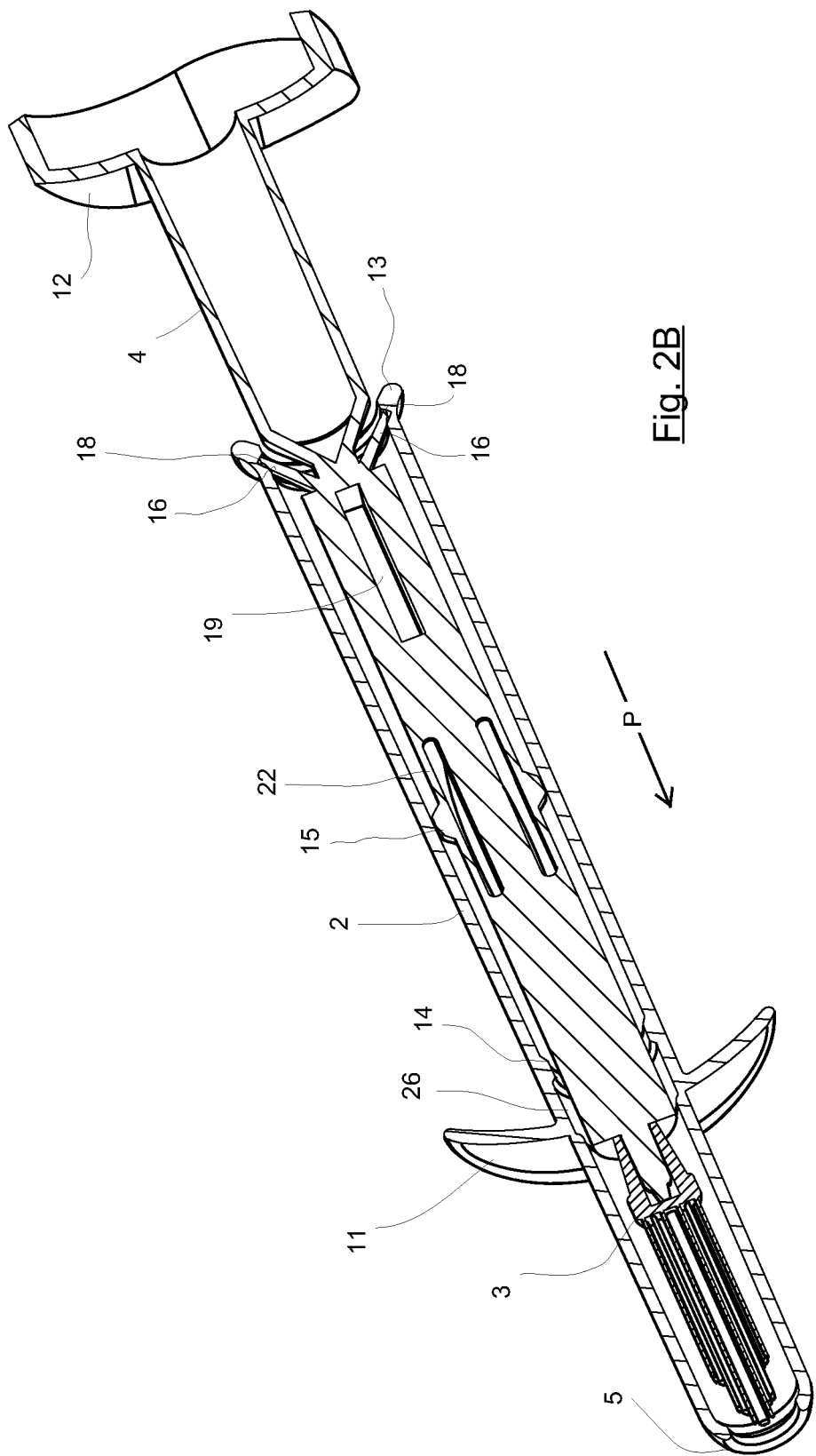

FIG. 2 shows a sampling device 1 according to the invention in the so-called introduction position and FIG. 3 shows the same sampling device 1 in the so-called sampling position. In the introduction position, the sample-collecting member 3—which, except for the first aspect of the invention, can be of any type—is retracted into the tube 2 and the sample-collecting member 3 is protected by the tube. In use, when the sampling device is in the introduction position, it is inserted into the mouth 93—see FIG. 7—of the vagina in the proximal direction P and pushed through the vagina 90, in particular the front portion 92 of the vagina 90, to the inside in the direction of the cervix 91. When the stop 11 comes to rest against the tissue 95 around the mouth 93 of the vagina, the proximal end of the tube 2 is situated in the deeper portion 94 of the vagina 90. With the sampling device according to the invention, the tube 2 may optionally also be shorter and still be in the front portion 92 of the vagina when the stop 11 rests against the tissue 95, for example if sampling of the front portion 92 of the vagina 90 is desired, but usually sampling of the cervix 91 and/or the deeper portion 94 of the vagina is desired.

During insertion, the tube 2 protects the mouth 93 of the vagina and the vagina 90 against the sampling member 3. This prevents the sample-collecting member from sampling the mouth 93 or the front portion 92 of the vagina 90, which could result in early saturation of the sample-collecting member and would thus compromise the reliability of the sample to be collected from the cervix 91. Furthermore, contact of the sample-collecting member 3 with the mouth 93 of the vagina or the vagina, for example the front portion 92 thereof, could be regarded as unpleasant. When a third party, such as a physician or assistant physician, carries out the sampling, contact between the sample-collecting member 3 and the mouth 93 of the vagina and vagina 90 can be prevented by operating accurately and optionally using an aid, such as a speculum. However, in the case of self-sampling this is difficult and not sufficiently reliable. Protection by means of the tube 2 during insertion is very important in the case of self-sampling to ensure reliability and is very advantageous in the case of sampling by a third party because the requirements with regard to accurate operation are less high and aids can be dispensed with.

With cantilever-like brush hairs, in particular elongate, axial brush hairs, there is the additional problem that, when the brush hairs become caught during the introduction procedure into the mouth 93 of the vagina or the vagina 90, this may not only be very unpleasant, but may also complicate or prevent introduction of the sampling device 1.

Figure 3A:
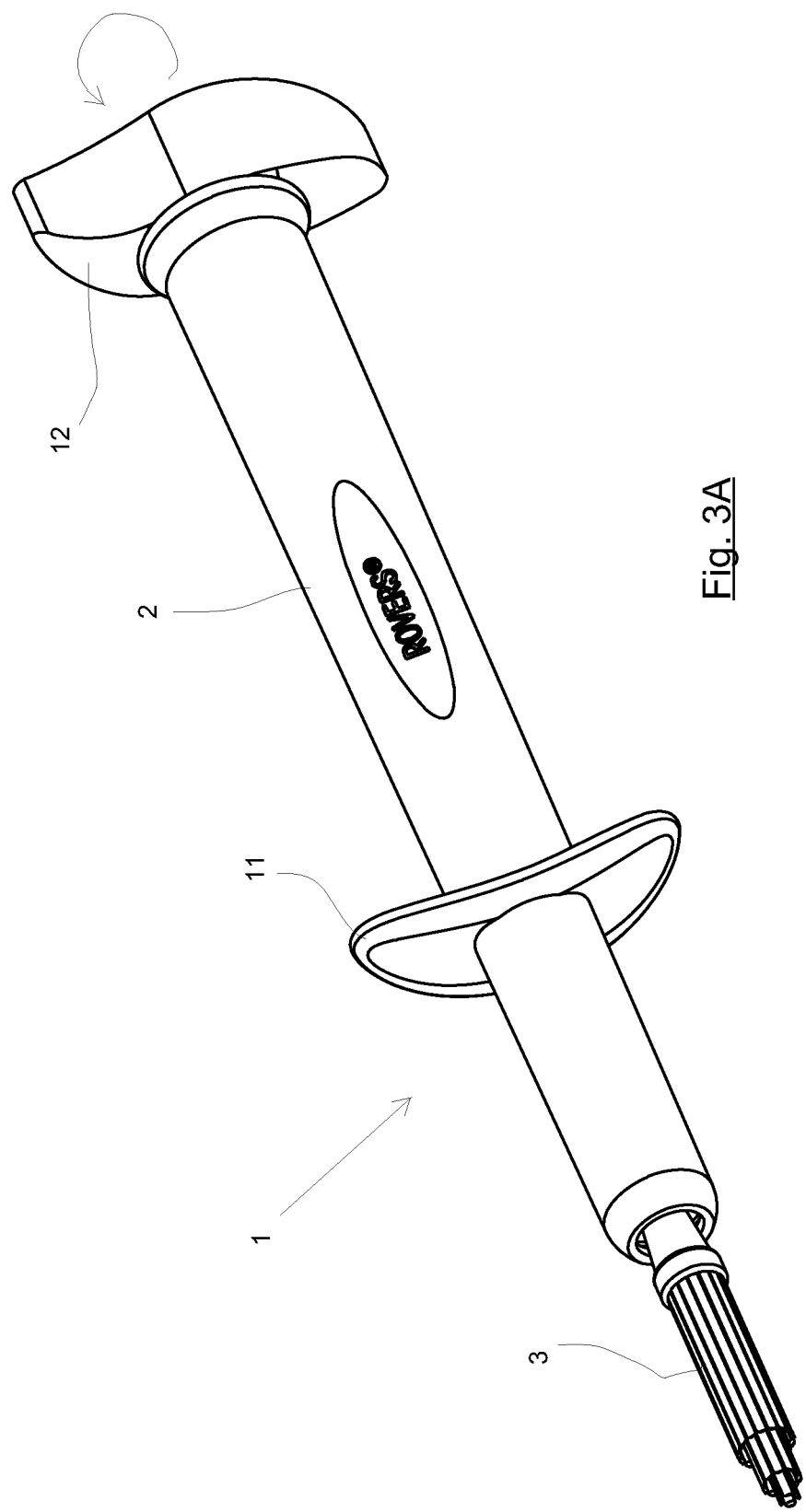
FIG. 3 shows the sampling device from FIGS. 1 and 2 in the sampling position, with FIG. 3A being a perspective view and FIG. 3B being a perspective longitudinal section.
Figure 7:
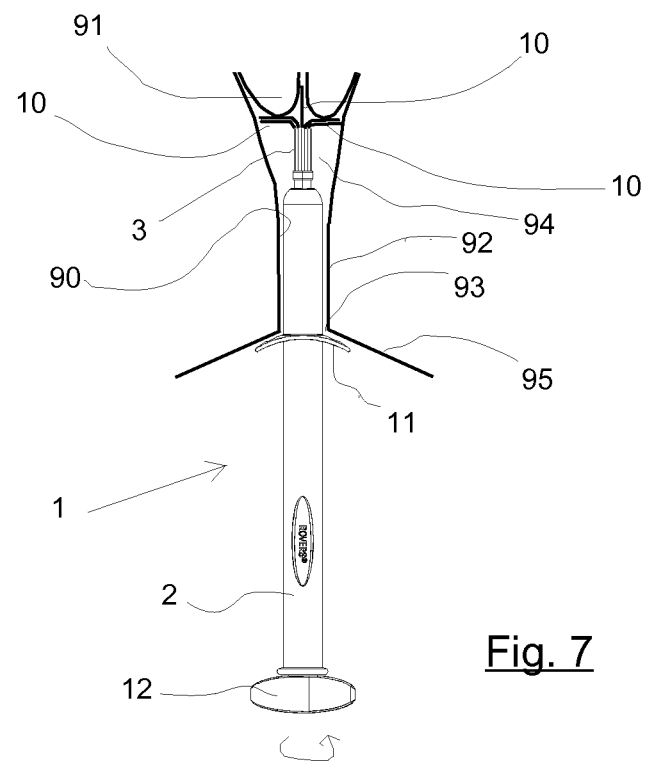
FIG. 7 shows a highly diagrammatical view of the use of the sampling device according to the invention during sampling of the vagina and/or cervix.

FIG. 3 and FIG. 7 show the sampling device 1 in the so-called sampling position. This sampling position is reached by sliding the plunger 4, from the introduction position shown in FIG. 2, in the distal direction D through the tube 2. The sample-collecting member 3 is then pushed out through the proximal tube end 5. After the sample-collecting member 3 has thus been pushed out, the sample-collecting member 3 is rotated by turning the plunger 4 around its longitudinal axis 27, as is indicated in FIG. 3a and FIG. 7 by means of arrows. A few rotations are necessary in order to produce a reliable sample. Generally, 3 turns are regarded as sufficient for a reliable sample. This number may, if desired, also be higher or lower.

In order to ensure that a sampling device 1 according to one or more aspects of the invention is introduced at the correct depth, the tube 2, according to the second aspect of the invention, is provided on the outside with an insertion stop 11, which—see FIG. 7—comes to rest against tissue next to the mouth 93 of the vagina. The insertion stop 11 is comprised of two opposite wing portions which together define an oval-like shape. This is advantageous in view of the geometry of the female body at the location of the mouth 93 of the vagina. The insertion depth X—see FIG. 1A—, measured as the distance from the insertion stop 11 to the proximal end 5 of the tube 2, may, inter alia, be dependent on the type of sampling member or the dimensions thereof. In general, this insertion depth X will be at least 30 mm, in particular 30 to 70 mm. With the sampling device as illustrated in FIGS. 1-7, the insertion depth X is approximately 50 mm. For an improved grip, in particular for the self-sampling woman, the distance Y—see FIG. 1A—from the insertion stop 11 up to the distal end of the tube is at least 5 cm, in particular at least 8 cm. In practice, this distance Y will be 8 to 15 cm. In the illustrated embodiment, this distance Y is approximately 9 cm.

Figure 3B:
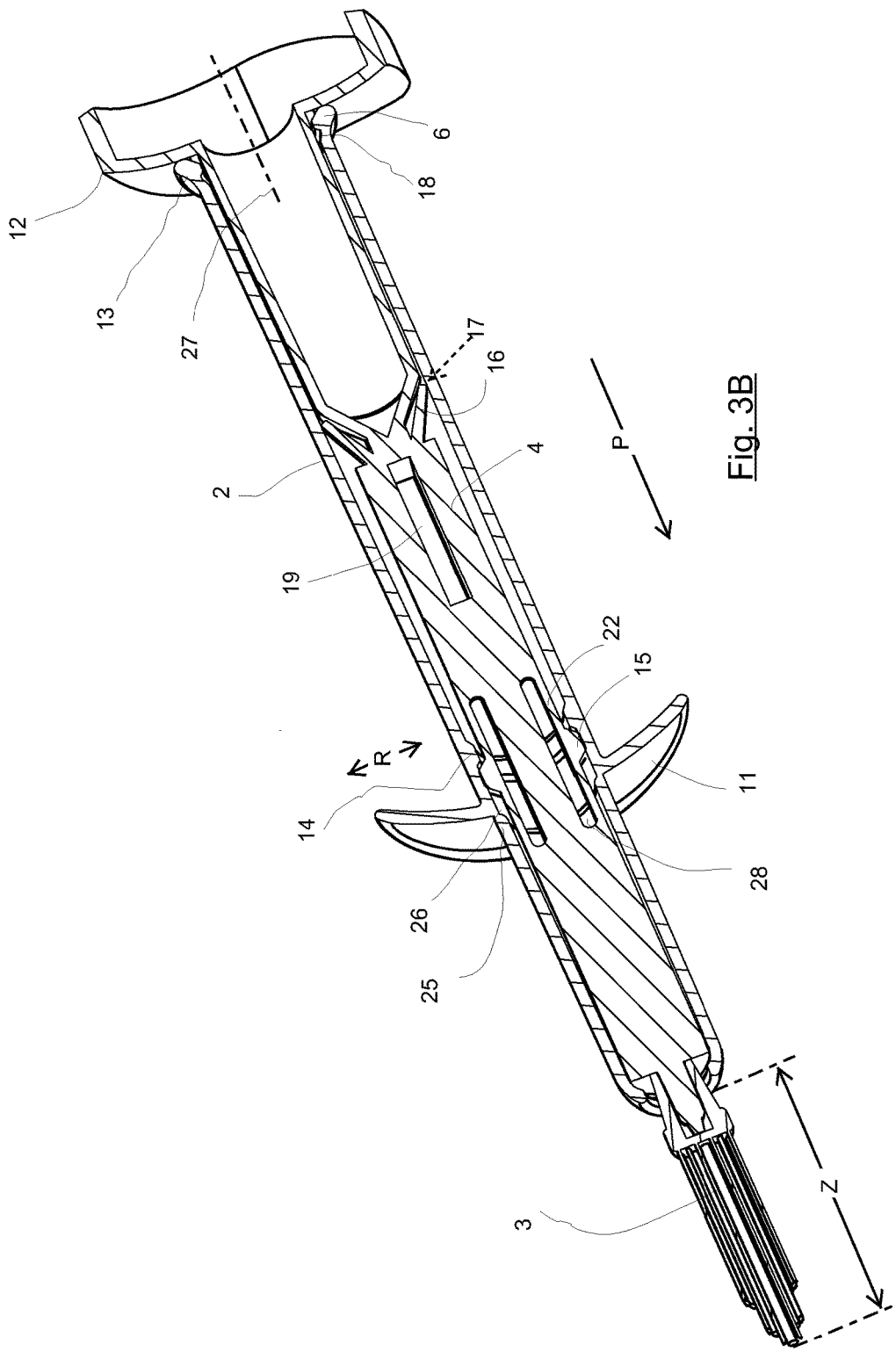

In order, on the one hand, to prevent the sample-collecting member from being extended too far or the plunger from being pushed too deep into the distal tube end and, on the other hand, in addition to the insertion stop 11, to accurately determine the insertion depth of the sampling member 3, the sampling device 1, according to the third aspect of the invention, is provided with an extension limiter which determines the maximum extension length Z—see FIG. 3b—over which the sample-collecting member 3 can be extended out of the proximal tube end 5. This extension length Z is measured from the proximal end of the sample-collecting member 3 up to the proximal tube end 5 and is at least 10 mm and in particular 10 to 45 mm. At an extension length of 10 mm or more, the sampling member is sufficiently far out of the tube to ensure good sampling. In the illustrated embodiment, the extension length is approximately 33 mm. When sampling the vagina in the region near the cervix or the cervix itself, the extension length will in particular be at most 35 mm.

According to the invention, the extension limiter can be produced in a simple manner by providing a widened section 12 at the distal plunger end 8. The widened section 12 extends, viewed from the axial axis 27 of the plunger, in the radial direction of the tube along a distance which is greater than the radius of the tube 2 at the location of the distal tube end 6. This ensures that the widened section 12 comes to rest against the edge 13 of the distal tube end 6 when the sample-collecting member 3 is extended in the proximal direction P. Instead of the widened section 12 or—as is illustrated in FIGS. 1-7—in addition to the widened section 12, the extension limiter may comprise an extension lock. Viewed in the extension direction of the longitudinal axis 27—also referred to as the axial direction —, the extension limiter fixes the relative position of the plunger 4 with respect to the tube 2 when the sample-collecting member 3 is extended over the maximum extension length Z.

During rotation of the plunger, when the sampling device is in the position illustrated in FIG. 7, the self-sampling woman can count the number of turns, in this case even the number of half turns, due to the elongate shape of the widened section 12, viewed transversely to the axial axis 27.

In FIGS. 1-7, the extension lock is produced by providing a rib 14 on the inside of the tube 2, which rib 14 extends in the peripheral direction of the tube and by providing a locking lug 15 on the plunger 4, which locking lug 15 protrudes in the radial direction. The locking lug 15 is provided on a resilient arm 22 which runs alongside a slot 28. The locking lug 15 can thus spring back in a radially inward direction in order to pass the rib 14 when the locking lug approaches the rib 14 from the distal side—this is the right-hand side of the rib in FIG. 3b—the plunger is sufficiently pushed in the proximal direction P. After the locking lug 15 has passed the rib 14, the locking lug will spring back again in the radially outward direction in order—as is shown in FIG. 3b—to engage with the recess 26 behind the rib 14 on the proximal side of the rib 14. At reference numeral 25, the tube narrows again. By moving this narrowing in the distal direction and—on the proximal side—close to the locking lug 15, the locking lug 15 is locked in the position illustrated in FIG. 3b in opposite axial directions. Thus, a combined extension limiter and extension lock would be achieved, in which case the widened section 12 as an extension limiter would be redundant. It will be clear that such an embodiment is also in accordance with the invention. Other embodiments of the extension lock and extension limiter are also readily possible according to the invention. It will furthermore be clear that, in the illustrated embodiment of the rib 14 and the locking lug 15 provided on a resilient arm 22, it is in principle also possible for the locking lug to pass, with radial compression, the rib 14 in the distal direction when the plunger 4 is moved from the position illustrated in FIG. 3b in the distal direction with respect to the tube 2.

In order to prevent, after assembly, the plunger 4 from inadvertently being pulled out of the tube 2, the sampling device 1, according to the fourth aspect of the invention, is provided with a disassembly restriction which is designed to prevent movement of the plunger 4 in the distal direction D with respect to the tube 2 when the sample-collecting member 3 is in a position in which it is completely retracted in the tube—for example in the introduction position. In the illustrated embodiments of the invention, the disassembly restriction is designed as a lip 16 provided on the plunger 4, which, from the plunger, points obliquely in the distal direction. Thus, the lip 16 can easily pass an internal obstacle in the tube 2 when the plunger 4 is pushed in the proximal direction into the distal tube end 6, but the lip 16 will catch behind this obstacle when the plunger is pushed back in the distal direction. With the embodiment illustrated in FIGS. 1-4, this obstacle is a groove 18 which is formed in the distal tube edge 13. With the embodiment of the sampling device according to the invention illustrated in FIG. 5, the obstacle is formed by the rib 114 of the extension lock. In this case, the rib 114 has a double function.

Referring to FIG. 3b, it will furthermore be clear that the lip 16 (or 116) can also act as an extension lock if a groove which is similar to groove 18 or a rib which is similar to rib 14 is provided at reference numeral 17 (FIG. 3b). The extension lock 14, 15 (114, 115 in FIG. 5) could then optionally be redundant.

In order to enable the sampled woman, such as the self-sampling woman or the woman sampled by a third party, to readily follow whether the sample-collecting member is being rotated sufficiently during sampling, in particular a sufficient number of times, the sampling device 1, according to the fifth aspect of the invention, is provided with a clicking mechanism which is designed to generate a tangible and/or audible click when the plunger 4 has been rotated through a predetermined angular distance, such as 180° or 360°, with respect to the tube 2.

With the embodiments of a sampling device according to the invention illustrated in the figures, the clicking mechanism is produced by providing a clicking bump 21 and a clicking lug 20. When the sampling device is in the sampling position, a tangible and/or audible click is produced as soon as the clicking lug 20 passes the clicking bump during rotation of the plunger 4 with respect to the tube 2. The clicking bump can in this case be, for example a clicking groove, such as a slot, or a clicking rib. When the clicking bump 21 is provided on the inside of the tube 2, the clicking lug is provided on the plunger 4, and conversely, when the clicking bump 21 is provided on the plunger, the clicking lug 20 is provided on inside of the tube 2.

Figure 4A:
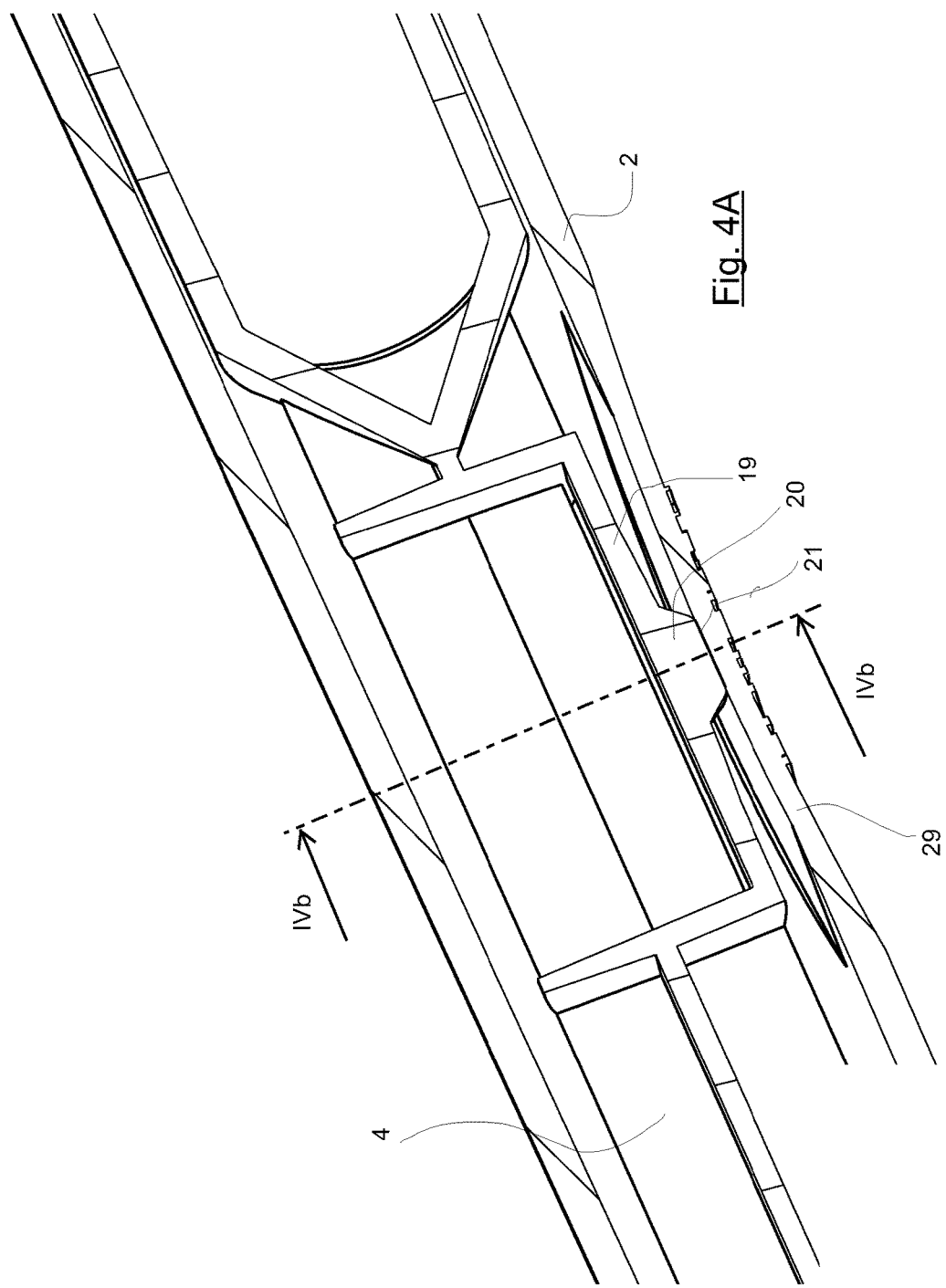
FIG. 4 shows a detail view of the clicking mechanism, with FIG. 4A showing a longitudinal section of a portion of the sampling device as a detail while it is in the sampling position and FIG. 4B showing a perspective cross-sectional view according to the arrows IVb from FIG. 4A.

In order to explain an embodiment of the clicking mechanism according to the invention in more detail, FIG. 4 shows two details of the sampling device 1 while the latter is in the sampling position illustrated in FIG. 3. With the illustrated clicking mechanism, the clicking lug 20 is provided on the plunger and the clicking bump is formed by a clicking groove 21 provided on the inner wall of the tube 2. The clicking lug 20 is provided on a resilient arm 19. When the clicking lug 20 approaches the flattened zone 29 during the rotation of the plunger 4 with respect to the tube 2, the resilient arm is pushed in slightly and the clicking lug 20 comes to lie under tension. As soon as the clicking lug 20 then reaches the groove 21, the clicking lug veers in the radially outward direction into the groove 21 in order shortly thereafter, when rotation is continued, to exit from the latter. This produces a click which is both audible and tangible to the sampled woman.

Figure 8:
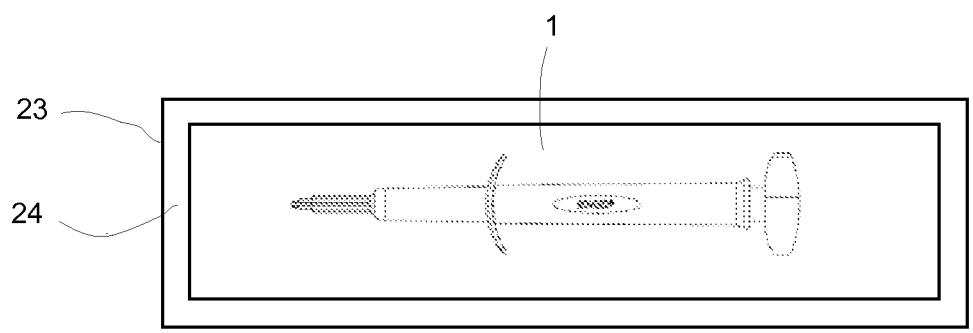
FIG. 8 shows a diagrammatical perspective view of a sampling device according to the invention packaged in sterile packaging.

Referring to FIG. 8, the sampling device 1 according to the invention is supplied packaged in a packaging 23 in a supply position. The packaging 23 is transparent on at least a side 24, so that the sampling device can be seen without having to open the packaging. The sampling device 1 is packaged in the packaging 23 in a sterile manner.

In the supply position illustrated in FIG. 8 and FIG. 1b, the sample-collecting member 3 protrudes from the tube 2. The woman to be sampled can then see the sample-collecting member 3, in the case of transparent packaging even without having to open the packaging, prior to sampling. This has a reassuring effect and increases the trust of the woman to be sampled. Before insertion, the plunger 4 will first be pushed in the distal direction with respect to the tube 2 in order to withdraw the sample-collecting member 3 from the tube 2. After correct insertion, the plunger will then be pushed in the proximal direction with respect to the tube in order to push the sample-collecting member out of the tube 2 again. Subsequently, the sample will be collected, following which the sampling device—optionally after having retracted the sample-collecting member back into the tube—is removed from the vagina. Then, the entire sampling device, only the sample-collecting member, or a portion of the sample which has been transferred from the sample-collecting member to a sample carrier can be sent to a laboratory for further examinations. The sampling device according to one or more aspects of the invention is particularly suited for tests for HPV infection, but can also be used for other examinations.

The supply position and sampling position can be identical. However, if an extension lock has been provided, then it is practical if, in the supply position, the plunger is not locked. With the embodiments illustrated in the figures, in the supply position, the locking lug 15 of the plunger 4 will therefore be situated on the distal side of the rib 14, in particular bear against the distal side of the rib 14. Thus, the plunger can be pushed unimpeded from the supply position to the introduction position illustrated in FIG. 2.

Various aspects of the present invention are described in more detail in the following clauses:

1] Sampling device for sampling a body cavity, in particular for sampling the vagina and/or cervix, in which the sampling device comprises:
- a tube having an open proximal tube end and an open distal tube end;
- a sample-collecting member;
- a plunger having a proximal plunger end and a distal plunger end;
- in which the plunger is inserted in the tube, with the distal plunger end protruding from the distal tube end, and carries the sample-collecting member at the proximal tube end;

in which the plunger is displaceable in the proximal direction in the tube from a retracted introduction position to an extended sampling position;
in which, in the introduction position, the sample-collecting member is situated inside the tube and protrudes from the tube in the sampling position;
in which the sample-collecting member comprises a carrier part and a plurality of brush hairs which protrude from the carrier part in the manner of a cantilever.

2] Sampling device according to clause 1, in which the plurality of brush hairs comprise elongate brush hairs protruding in the proximal direction.

3] Sampling device according to clause 2, in which said elongate brush hairs have a length of at least 15 mm, such as 17-35 mm.

4] Sampling device for sampling a body cavity, in particular for sampling the vagina and/or cervix, in which the sampling device comprises:
- a tube having an open proximal tube end and an open distal tube end;
- a sample-collecting member;
- a plunger having a proximal plunger end and a distal plunger end;
- in which the plunger is inserted in the tube, with the distal plunger end protruding from the distal tube end, and carries the sample-collecting member at the proximal tube end;
- in which the plunger is displaceable in the proximal direction in the tube from a retracted introduction position to an extended sampling position;
- in which, in the introduction position, the sample-collecting member is situated inside the tube and protrudes from the tube in the sampling position; and
- in which the tube is provided on the outside with a radially protruding insertion stop which defines the insertion depth over which the tube can be introduced into the body cavity, in particular the vagina, in the proximal direction.

5] Sampling device according to clause 4 in combination with one of clauses 1-3.

6] Sampling device according to clause 4 or 5, in which the insertion depth, measured as the distance from the insertion stop to the proximal end of the tube, is at least 30 mm, in particular 30 to 70 mm, such as approximately 50 mm.

7] Sampling device according to one of clauses 4-6, in which the distance from the insertion stop to the distal end of the tube is at least 5 cm, in particular at least 7 cm, and more particularly 7 to 15 cm, such as 8 to 10 cm.

8] Sampling device for sampling a body cavity, in particular for sampling the vagina and/or cervix, in which the sampling device comprises:
- a tube having an open proximal tube end and an open distal tube end;
- a sample-collecting member;
- a plunger having a proximal plunger end and a distal plunger end;
- in which the plunger is inserted in the tube, with the distal plunger end protruding from the distal tube end, and carries the sample-collecting member at the proximal tube end;
- in which the plunger is displaceable in the proximal direction in the tube from a retracted introduction position to an extended sampling position;
- in which, in the introduction position, the sample-collecting member is situated inside the tube and protrudes from the tube in the sampling position; and
- in which the sampling device is provided with an extension limiter which defines a maximum extension length over which the sample-collecting member can be extended from the proximal tube end.

9] Sampling device according to clause 8 in combination with one of clauses 1-7.

10] Sampling device according to clause 8 or 9, in which, measured from the proximal end of the sample-collecting member to the proximal tube end, said extension length is at least 10 mm, in particular 10 to 45 mm, such as 25 to 35 mm.

11] Sampling device according to one of clauses 8-10, in which the extension limiter comprises a widened section on the distal plunger end, which widened section comes to a halt against the distal tube end when the sample-collecting member is extended in the proximal direction.

12] Sampling device according to clause 11, in which the widened section has a shape which is non-round with respect to the axial axis of the plunger—such as a shape which is elongate, viewed transversely to the axial axis.

13] Sampling device according to one of clauses 8-12, in which the extension limiter comprises an extension lock which, viewed in the axial direction of the plunger, fixes the relative position of the plunger with respect to the tube at the maximum extension length.

14] Sampling device according to clause 13, in which the extension lock comprises:
- a rib provided inside the tube and extending in the peripheral direction of the tube; and
- a locking lug provided on the plunger and protruding in the radial direction;

the locking lug being resilient and flexible in the radial direction in order to pass the rib in the axial direction.

15] Sampling device according to clause 13, in which the extension lock comprises:
- a lip which runs at an angle with respect to the axial direction and has a free end and a fixed end which is attached to one of either the tube or the plunger;
- a first groove in which the free end of said lip can be accommodated and which is provided in the other of either the plunger or the tube.

16] Sampling device for sampling a body cavity, in particular for sampling the vagina and/or cervix, in which the sampling device comprises:
- a tube having an open proximal tube end and an open distal tube end;
- a sample-collecting member;
- a plunger having a proximal plunger end and a distal plunger end;
- in which the plunger is inserted in the tube, with the distal plunger end protruding from the distal tube end, and carries the sample-collecting member at the proximal tube end;
- in which the plunger is displaceable in the proximal direction in the tube from a retracted introduction position to an extended sampling position;

in which, in the introduction position, the sample-collecting member is situated inside the tube and protrudes from the tube in the sampling position;
in which the sampling device is provided with a disassembly restriction, comprising:
   a lip which runs at an angle with respect to the axial direction and has a free end and a fixed end which is attached to one of either the tube or the plunger;
   a second groove in which the free end of said lip can be accommodated and which is provided in the other of either the plunger or the tube.

17] Sampling device according to clause 16 in combination with one of clauses 1-15.

18] Sampling device for sampling a body cavity, in particular for sampling the vagina and/or cervix, in which the sampling device comprises:
   a tube having an open proximal tube end and an open distal tube end;
   a sample-collecting member;
   a plunger having a proximal plunger end and a distal plunger end;
in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position;
in which the sampling device is furthermore provided with a clicking mechanism which is designed to generate a click when the plunger is rotated through a predetermined angular distance, such as 180° or 360°, with respect to the tube.

19] Sampling device according to clause 18 in combination with one of clauses 1-17.

20] Sampling device according to clause 18 or 19, in which the clicking mechanism comprises a clicking bump, such as a clicking groove or clicking rib, and a radial clicking lug, with the clicking bump being provided on one of either the tube or the plunger and the clicking lug on the other of either the plunger or the tube, in order to generate said click in the sampling position when, during rotation of the plunger with respect to the tube, the clicking lug passes the clicking bump.

21] Sampling device for sampling a body cavity, in particular for sampling the vagina and/or cervix, in which the sampling device comprises:
   a tube having an open proximal tube end and an open distal tube end;
   a sample-collecting member;
   a plunger having a proximal plunger end and a distal plunger end;
   a packaging;
in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position.

22] Sampling device according to clause 21 in combination with one of clauses 1-20.

23] Sampling device according to clause 21 or 22, in which the sampling device has a supply position, in which the plunger protrudes from the proximal tube end, preferably substantially outside the tube;
in which the plunger is displaceable in the distal direction with respect to the tube from the supply position to said introduction position; and
in which the sampling device is packaged in the packaging in the supply position, the packaging preferably being packaged in a sterile manner.

24] Sampling device according to one of clauses 21-23, in which the packaging is transparent.

25] Sampling device for sampling a body cavity, in particular for sampling the vagina and/or cervix, in which the sampling device comprises:
   a tube having an open proximal tube end and an open distal tube end;
   a sample-collecting member;
   a plunger having a proximal plunger end and a distal plunger end;
in which the plunger is inserted in the tube, with the distal plunger end protruding from the distal tube end, and carries the sample-collecting member at the proximal tube end;
in which the plunger is displaceable in the proximal direction in the tube from a retracted introduction position to an extended sampling position;
in which, in the introduction position, the sample-collecting member is situated inside the tube and protrudes from the tube in the sampling position;
in which the outside of the tube, at least the outside of the tube in the part of the tube which is proximal to the insertion stop, is provided with a slippery layer.

26] Sampling device according to clause 25 in combination with one of clauses 1-24.

27] Method for preparing the sampling device according to one of the preceding clauses 21-24, comprising the following steps:
   an unwrapping step in which the sampling device is removed from the packaging;
   an inspection step in which the sampling member, before or after the unwrapping step, is inspected by the patient to be sampled, with the sampling member protruding from the tube during the inspection step;
   a retraction step in which the sampling member, by displacing the plunger in the distal direction with respect to the tube, is retracted into the tube into said introduction position, with the retraction step taking place after the inspection step.

As will be clear to those skilled in the art, many variants are conceivable without departing from the scope of the above clauses. Thus, for example, the insertion stop, the extension limiter, the sampling member, the disassembly restriction, and the clicking mechanism can be designed in various ways without departing from the scope of the clauses. With various aspects of the invention, the sampling member may, for example, be designed as an absorbing body without brush hairs or with limp, non-cantilever-like brush hairs.

In FIG. 7, it can be seen that, at least a portion of the axial, cantilever-like hairs 10, can bend approximately midway and comes up against the cervix during sampling. Thus, the cervix and the surrounding area are sampled efficiently. The central brush hairs 10 or, if desired, a dedicated central part of the sample-collecting member can in this case protrude into the cervical canal in order to also sample the inside thereof. According to the invention, however, it is not strictly necessary to sample the cervix when sampling for HPV. Sampling of other tissue from the vagina 94, preferably in the vicinity of the cervix, also suffices. The illustration in FIG. 7 therefore serves as an illustration for use and does not show in any way how sampling takes place. If, for example, the sampling device 1 in FIG. 7 is not aligned properly with the cervix, which is quite possible in the case of self-sampling, the sample will, according to the invention, be collected elsewhere in the vagina, usually in the vicinity of the cervix.

The invention claimed is:

1. A sampling device for sampling a body cavity, the sampling device comprising:
   a tube having an open proximal tube end and an open distal tube end;
   a sample-collection member;
   a plunger having a proximal plunger end, a distal plunger end, and an axial direction; and
   an extension limiter,
   wherein the plunger is inserted in the tube, with the distal plunger end protruding from the distal tube end, and the plunger carries the sample-collection member at the proximal tube end,
   the plunger is displaceable in a proximal direction in the tube from a retracted introduction position to an extended sampling position,
   a distal direction is opposite the proximal direction,
   in the introduction position, the sample-collection member is situated inside the tube,
   in the sampling position, the sample-collection member protrudes from the tube and is rotatable, when inside the body cavity, to collect a tissue sample on the sample-collection member,
   the extension limiter defines a maximum extension length over which the sample-collection member can be extended from the proximal tube end,
   the extension limiter comprises an extension lock which, viewed in the axial direction of the plunger and when the plunger is in the extended sampling position, is configured to fix a relative position of the plunger from movement toward the distal tube end of the tube, the sample-collection member being extended the maximum extension length from the proximal tube end when the plunger is in the extended sampling position, the sample-collection member is configured to be rotatable a number of 360 degree revolutions by rotating the plunger with respect to the tube whilst simultaneously the relative position of the plunger with respect to the tube is fixed by the extension lock.

2. The sampling device of claim 1, wherein the tube comprises a peripheral direction and a radial direction, and the extension lock comprises:
   a rib provided inside the tube and extending in the peripheral direction of the tube; and
   a locking lug provided on the plunger and protruding in the radial direction, the locking lug being resilient and flexible in the radial direction in order to pass the rib in the axial direction.

3. The sampling device of claim 1, wherein the extension lock comprises:
   a lip that runs at an angle with respect to the axial direction and has a free end and a fixed end that is attached to a first one of either the tube or the plunger; and
   an internal obstacle positioned in the tube, the free end of the lip being configured to pass by the obstacle when the plunger is pushed in the proximal direction and to catch behind the obstacle when the plunger is pushed in the distal direction and the obstacle is provided in a different second one of either the tube or the plunger.

4. The sampling device of claim 1, wherein,
   measured from a proximal end of the sample-collection member to the proximal tube end, the maximum extension length is at least 10 mm.

5. The sampling device of claim 1, wherein the extension limiter comprises a widened section on the distal plunger end, the widened section coming to a halt against the distal tube end when the sample-collection member is extended in the proximal direction.

6. The sampling device of claim 5, wherein the plunger has an axial axis, and the widened section has a shape that is non-round with respect to the axial axis of the plunger.

7. The sampling device of claim 1, further comprising:
   a clicking mechanism that is designed to generate a click when the plunger is rotated through a predetermined angular distance with respect to the tube.

8. The sampling device of claim 7, wherein the clicking mechanism comprises a clicking bump, and a radial clicking lug, with the clicking bump being provided on the inside of the tube or on the plunger, and the clicking lug being provided on the other of the plunger or the inside of the tube, in order to generate the click in the sampling position when, during rotation of the plunger with respect to the tube, the clicking lug passes the clicking bump.

9. The sampling device of claim 1, wherein the sample-collection member comprises a carrier part and a plurality of brush hairs that protrude from the carrier part in the manner of a cantilever.

10. The sampling device of claim 9, wherein the plurality of brush hairs comprise elongate brush hairs protruding in the proximal direction.

11. The sampling device of claim 10, wherein the elongate brush hairs have a length of at least 15 mm.

12. The sampling device of claim 1, wherein the tube comprises an outside with a radially protruding insertion stop that defines an insertion depth over which the tube can be introduced into the body cavity in the proximal direction.

13. The sampling device of claim 12 for use with the body cavity being a vagina, wherein the insertion stop is designed to come to a halt against external tissue around a mouth of the vagina when the sampling device is pushed into the vagina in a direction of a cervix.

14. The sampling device of claim 12, wherein the insertion depth, measured as a distance from the insertion stop to the proximal tube end of the tube, is at least 30 mm.

15. The sampling device of claim 12, wherein a distance from the insertion stop to the distal tube end of the tube is at least 5 cm.

16. The sampling device of claim 1, further comprising:
   a disassembly restriction that is designed to prevent movement of the plunger in the distal direction with respect to the tube when the sample-collection member is completely retracted in the tube.

17. The sampling device of claim 16, wherein the disassembly restriction comprises:
   a lip that runs at an angle with respect to the axial direction and has a free end and a fixed end that is attached to one of either the tube or the plunger; and
   a second groove in which the free end of the lip can be accommodated and which is provided in the other of either the plunger or the tube.

18. The sampling device of claim 1, further comprising a packaging, wherein the sampling device has a supply position, in which the plunger protrudes from the proximal tube end, the plunger is displaceable in the distal direction with respect to the tube from the supply position to the introduction position, and the sampling device, situated in the supply position, is packaged in the packaging in a sterile manner.

19. The sampling device of claim 18, wherein the packaging is transparent.

20. The sampling device of claim 1, wherein the tube comprises an outside with a radially protruding insertion stop that defines an insertion depth over which the tube can be introduced into the body cavity in the proximal direction, and at least a portion of the outside of the tube that is proximal to the insertion stop is provided with a slippery layer.

21. The sampling device of claim 1, wherein the extension lock is inside the tube.

22. The sampling device of claim 1, wherein the sample-collection member comprises brush hairs.

23. A method of preparing a sampling device packaged in packaging, the sampling device comprising a tube, a sample-collection member, a plunger, and an extension limiter, the tube having an open proximal tube end and an open distal tube end, the plunger having a proximal plunger end, a distal plunger end, and an axial direction, wherein the plunger is inserted in the tube, with the distal plunger end protruding from the distal tube end, the plunger carries the sample-collection member at the proximal tube end, the plunger is displaceable in a proximal direction in the tube from a retracted introduction position to an extended sampling position, a distal direction is opposite the proximal direction, the sample-collection member is situated inside the tube when the plunger is in the introduction position, the sample-collection member protrudes from the tube and is rotatable, when in contact with the inside of a body cavity, to collect a tissue sample, from inside the body cavity, on the sample-collection member when the plunger is in the sampling position, the extension limiter defines a maximum extension length over which the sample-collection member can be extended from the proximal tube end, the extension limiter comprises an extension lock which, viewed in the axial direction of the plunger and when the plunger is in the extended sampling position, is configured to fix a relative position of the plunger from movement toward the distal tube end of the tube, the sample-collection member being extended the maximum extension length from the proximal tube end when the plunger is in the extended sampling position, the sample-collection member is configured to be rotatable a number of 360 degree revolutions by rotating the plunger with respect to the tube whilst simultaneously the relative position of the plunger with respect to the tube is fixed by the extension lock, the method comprising:

removing the sampling device from the packaging;

inspecting, by a patient to be sampled, the sample-collection member, before or after the sampling device is removed from the packaging, the sample-collection member protruding from the tube when inspected by the patient; and displacing the plunger in the distal direction with respect to the tube to retract the sample-collection member into the tube and move the plunger into the retracted introduction position after the sample-collection member has been inspected by the patient.

24. A sampling device for sampling a body cavity, the sampling device comprising:

a tube having an open proximal tube end facing in a proximal direction and an open distal tube end facing in a distal direction;

a sample-collection member;

a plunger having a proximal plunger end, a distal plunger end, and an axial direction; and an extension limiter, wherein the plunger is inserted in the tube, with the distal plunger end protruding from the distal tube end, and the plunger carries the sample-collection member at the proximal tube end, the plunger is displaceable in the proximal direction in the tube from a retracted introduction position to an extended sampling position, in the introduction position, the sample-collection member is situated inside the tube, in the sampling position, the sample-collection member protrudes from the tube and is rotatable, when inside the body cavity, to collect a tissue sample on the sample-collection member, the extension limiter defines a maximum extension length over which the sample-collection member can be extended from the proximal tube end, the extension limiter comprises an extension lock which, viewed in the axial direction of the plunger and when the plunger is in the extended sampling position, is configured to fix, when the sample-collection member is extended at the maximum extension length from the proximal tube end, a relative position of the plunger with respect to the tube such that the plunger is prevented from movement towards the distal tube end, the plunger and the sample-collection member are configured to rotate when the plunger is in the extended sampling position, and the sample-collection member rotates a number of 360 degree revolutions when the plunger is rotated by the number of 360 degree revolutions with respect to the tube whilst simultaneously the relative position of the plunger with respect to the tube is fixed by the extension lock.

* * * * *